US00PP28184P3

(12) United States Plant Patent
Suphachadiwong

(10) Patent No.: US PP28,184 P3
(45) Date of Patent: Jul. 11, 2017

(54) ***VANDA* PLANT NAMED 'SPCDW1403'**

(50) Latin Name: ***Vanda* spp. Jones ex R. Br.**
Varietal Denomination: SPCDW1403

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Bangphra (TH)

( * ) Notice: Subject to any disclaimer, the term of this patent is extended or adjusted under 35 U.S.C. 154(b) by 55 days.

(21) Appl. No.: 14/756,773

(22) Filed: Oct. 9, 2015

(65) Prior Publication Data

US 2016/0120090 P1 Apr. 28, 2016

(30) Foreign Application Priority Data

Oct. 27, 2014 (QZ) ..... PBR 2014/2632

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — June Hwu
(74) *Attorney, Agent, or Firm* — Samuel R. McCoy, Jr.

(57) ABSTRACT

A new and distinct *Vanda* cultivar named 'SPCDW1403' which is characterized by the combination of a light cream-yellow flower with light brown spotting of both the sepals and petals, an undulating sepal and petal margins, and the stability of all characteristics from generation to generation. The new variety is a *Vanda*, typically produced as an indoor ornamental plant.

3 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1403'.

CROSS REFERENCE TO RELATED APPLICATIONS

This application claims priority to the Community Plant Variety Rights application number 2014/2632, filed Oct. 27, 2014, which is herein incorporated by reference.

BACKGROUND OF THE INVENTION

Parentage: The *Vanda* variety 'SPCDW1403' is the result of a planned breeding program. The new variety originated as a seedling from the crossing of the unpatented, proprietary seed parent *Vanda* 'A169' with the unpatented, proprietary pollen parent referred to as *Vanda* 'JBP'. The crossing was made by the inventor in his research greenhouse in Chonburi, Thailand in October of 2002.

The new variety was first selected by the inventor, Thumrong Suphachadiwong, a citizen of Thailand, in April of 2007, in a research greenhouse belonging to the inventor in Chonburi, Thailand. After identifying the new variety as a potentially interesting selection, the inventor continued confidential testing and propagation of 'SPCDW1403', assessing stability of the unique characteristics of this variety.

Asexual Reproduction: Asexual reproduction of the new cultivar 'SPCDW1403' was first initiated at a commercial laboratory belonging to the inventor in Chonburi, Thailand by tissue culture in April of 2008, with the first mericlones so reproduced flowering in 2013. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'SPCDW1403' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1403'. These characteristics in combination distinguish 'SPCDW1403' as a new and distinct *Vanda* cultivar:

1. *Vanda* 'SPCDW1403' exhibits a light cream-yellow flower; and,
2. *Vanda* 'SPCDW1403' exhibits a unique light brown spotting pattern of the sepals and petals; and,
3. *Vanda* 'SPCDW1403' exhibits strong undulation of both the sepal and petal margins.

BOTANICAL DESCRIPTION OF THE PLANT

Figure 1:
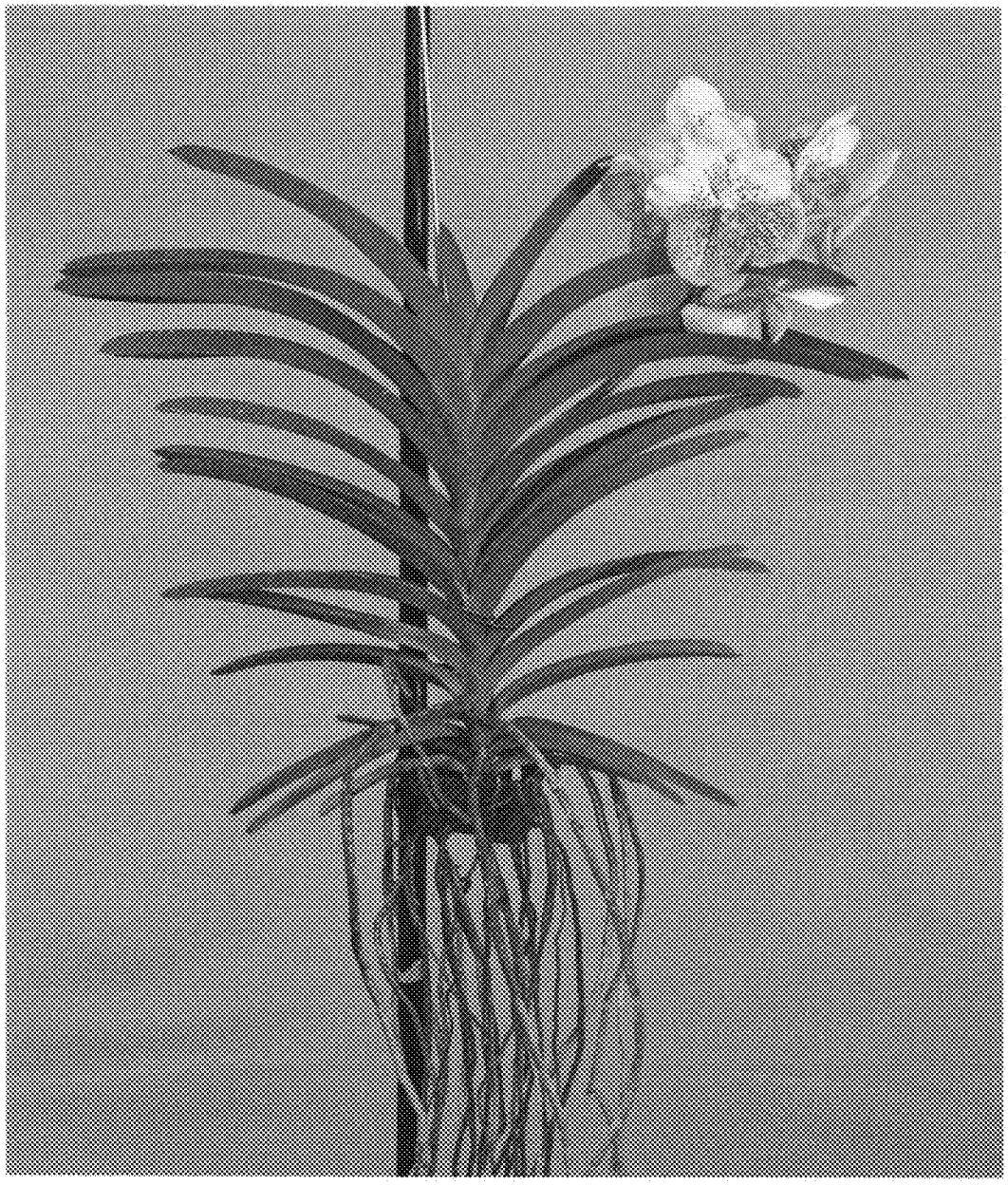
FIG. 1 illustrates, as nearly true as it is reasonably possible to make the same in color photographs of this type, an exemplary plant of 'SPCDW1403' grown in a commercial greenhouse in Honselersdijk, the Netherlands. This plant is approximately 5 years old, shown planted in an 8 by 8 cm container.
Figure 2:
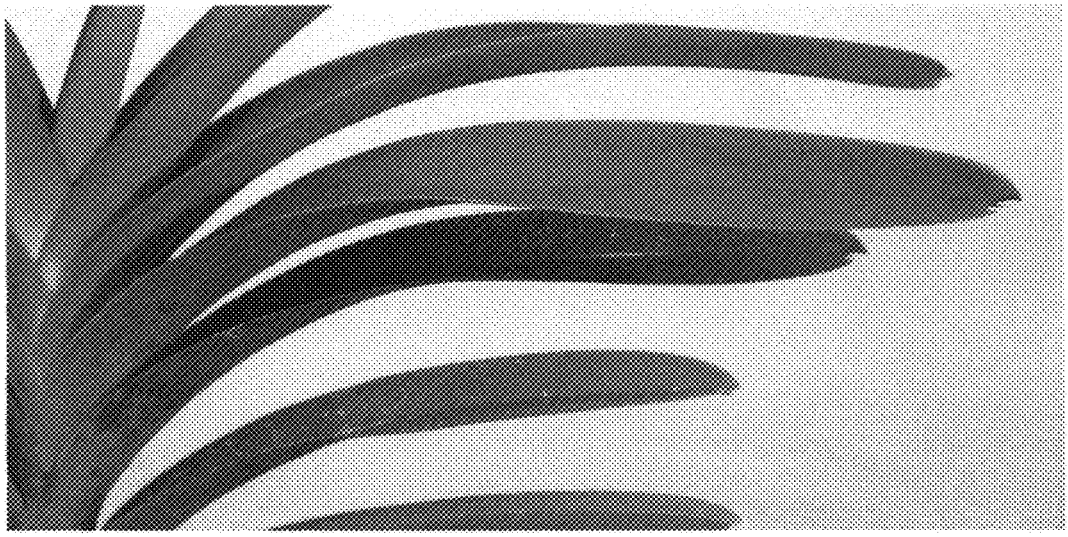
FIG. 2 illustrates, as nearly true as it is reasonably possible to make the same in color photographs of this type, the typical foliage of 'SPCDW1403'.
Figure 3:
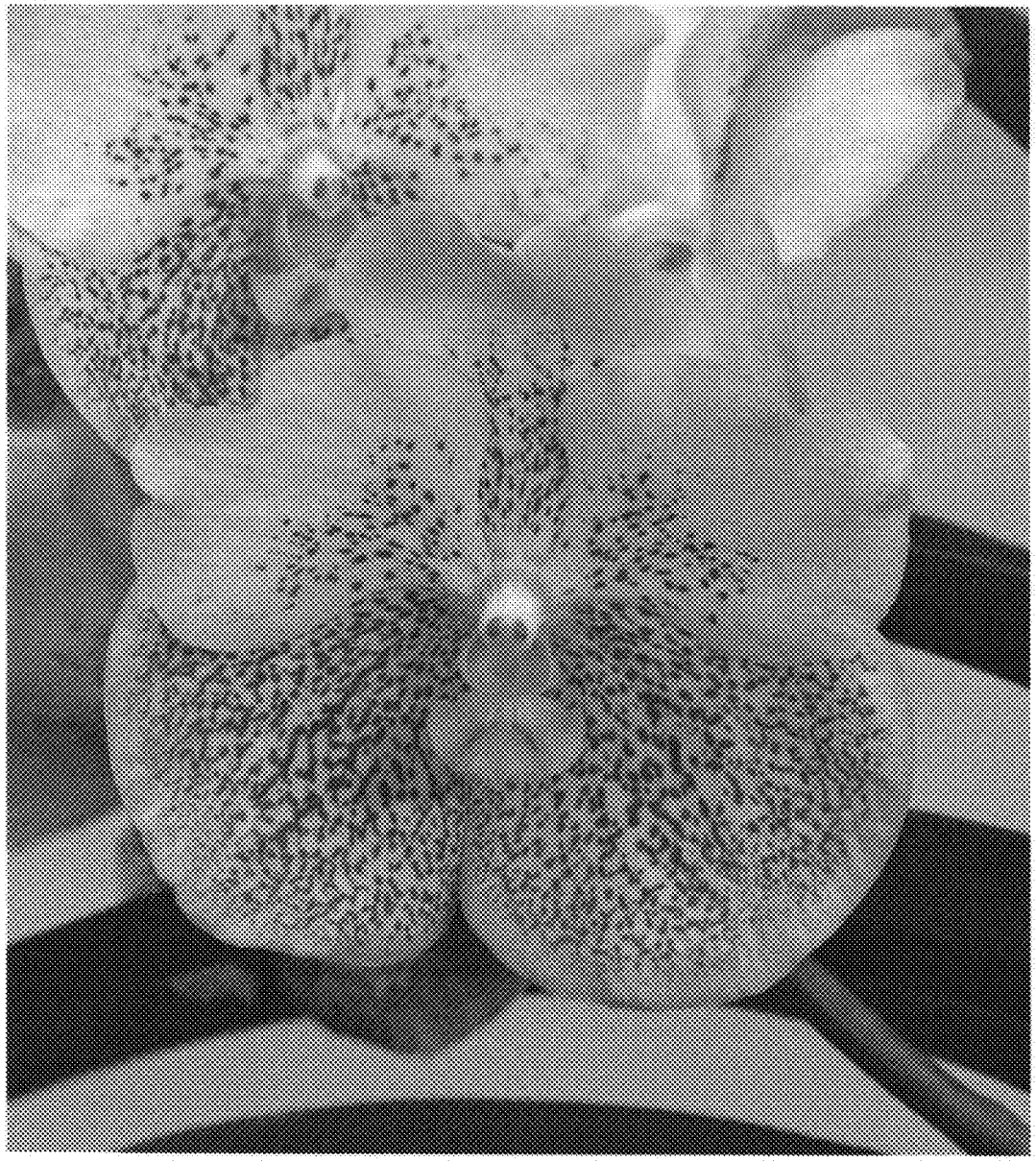
FIG. 3 illustrates, as nearly true as it is reasonably possible to make the same in color photographs of this type, the typical flowers of 'SPCDW1403'.

The following observations and measurements describe a five year-old 'SPCDW1403' plant grown in a greenhouse in Honselersdijk, the Netherlands. Temperatures ranged were approximately 23 degrees Celsius during the day and 19 degrees Celsius at night. No photoperiodic or chemical treatments were given to the plants. When natural lighting fell below 150 Watt, artificial lighting is given at 10,000 lux for 16 hours a day.

Those skilled in the art will appreciate that certain characteristics will vary with older or, conversely, with younger plants. 'SPCDW1403' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 (fifth edition).

A botanical description of 'SPCDW1403' and comparisons with other varieties of *Vanda* are provided below.

Plant description:

- *Growth habit*.—Monopodial, upright.
- *Average height from base (plant grown in hanging basket, so no soil line present) to top of foliage*.—45.6 cm.
- *Average height from base (plant grown in hanging basket, so no soil line present) to top of flowers*.—46.8 cm.
- *Plant spread*.—Average of 54.3 cm.
- *Normal pot size*.—Hanging basket (8 by 8 cm, square).
- *Growth rate*.—Moderate.
- *Propagation type*.—Meristematic tissue culture propagation using the base of the leaves.
- *Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease resistance*.—Good resistance to the normal diseases found in *Vanda*.
- *Drought tolerance and cold tolerance*.—Drought tolerance is typical for species. Superior cold tolerance, to approximately 6 degrees Celsius.

Root system:

- *General*.—Moderate to heavy rooting with aerial roots only located at the base of the stem, growing from approximately the lowest 25 percent of the stem. Roots very fleshy, non-fibrous. Mature roots becoming woody and inactive.
- *Diameter, juvenile roots*.—0.5 cm, on average.
- *Dimensions, mature roots*.—75.5 cm long with a diameter of 0.3 cm, on average.
- *Color, root apex*.—Yellow-Green RHS 143C.
- *Color, juvenile roots*.—Greyed-Green, near RHS 192A to 192B.
- *Color, mature roots*.—Yellow-Green RHS 146A to 146B.

Foliage:

- *Arrangement*.—Distichous.
- *Quantity*.—29 leaves, on average.
- *Dimensions*.—26.9 cm long and 2.8 cm wide, on average.
- *Shape of blade*.—Ligulate; curved downward; strongly carinate.
- *Aspect*.—Moderately curved.
- *Apex*.—Unequal praemorse.
- *Base*.—Sheathing.
- *Sheath dimensions*.—2.3 cm long ad 1.7 cm wide, on average.
- *Sheath color*.—Yellow-Green RHS 144A to 144B.
- *Margin*.—Entire.
- *Texture of top surface*.—Glabrous, matte.
- *Texture of bottom surface*.—Glabrous, matte.
- *Color*.—Juvenile foliage, adaxial surface — Yellow-Green RHS 144A; darker toward the margins, near Green RHS 143A. Juvenile foliage, abaxial surface — Approximates to a combination of Green RHS 143B and Yellow-Green RHS 144A; darker toward the margins, near Green RHS 143A. Mature foliage, adaxial surface — Green, nearest to RHS 137B. Mature foliage, abaxial surface — Yellow-Green RHS 144A.
- *Venation*.—Parallel.
- *Venation coloration*.—Yellow-Green RHS 144A on both the adaxial and abaxial surfaces.
- *Petiole*.—No petioles present, leaves sessile.

Inflorescence:

- *Flowers per stem*.—Average of 11.
- *Inflorescence arrangement*.—Axially placed raceme.
- *Inflorescence height*.—Approximately 22.5 cm (measured from base of lowest flower to top of upper flower).
- *Inflorescence width*.—Approximately 17.0 cm.
- *Peduncle*.—Length — Approximately 31.3 cm. Width — Approximately 0.7 cm. Aspect — Approximately 35° angle to rosette. Strength — Strong. Texture — Glabrous and very slightly glossy. Color — Yellow-Green RHS 144A.

Bud:

- *Rate of opening*.—Buds open approximately three weeks from first sight.
- *Length*.—Average of 1.8 cm.
- *Diameter*.—Average of 1.8 cm.
- *Shape*.—Broad obovate to near globose.
- *Color*.—In between Yellow-Green RHS 154B and Greyed-Green 160B.

Flower:

- *Flower type*.—Zygomorphic (orchidaceous), typical shape for the genus *Vanda*.
- *Shape*.—Zygomorphic, consisting of three sepals and three petals, one of which is transformed into a labellum; the two lateral petals heavily overlap the dorsal sepal and the lateral sepals; lateral sepals moderately overlap one another and also the dorsal sepal.

*Length* (*height*).—Approximately 9.7 cm.

*Width*.—Approximately 8.9 cm.

*Depth*.—Approximately 3.7 cm.

*Fragrance*.—No fragrance.

*Persistent*.—No.

*Quantity of petals*.—3; two conventional petals and one labellum.

*Petals*.—Arrangement — One lateral petal on each side. Length — Approximately 4.6 cm. Width — Approximately 4.4 cm. Shape — Broad ovate to near orbicular. Apex — Obtuse. Base — Cuneate. Margin — Entire; strongly undulated. Texture of upper forward surface — Glabrous, matte, velvety. Texture of lower back surface — Glabrous, matte, velvety. Color when opening, forward surface — Yellow, near RHS 3D, and tinged with Greyed-Yellow RHS 160B near the apex; finely dotted with Red-Purple RHS 59A to 59B at the base. Color when opening, back surface — Yellow, near RHS 3D, and tinged with Greyed-Yellow RHS 160B near the apex. Color when fully opened, forward surface — Yellow, near RHS 3D, and slightly darker at the margins, near RHS 6D; tinged with Greyed-Yellow RHS 160B near the apex; finely dotted with Red-Purple RHS 59A to 59B at the base. Color when fully opened, back surface — Yellow, near RHS 3D, and slightly darker at the margins, near RHS 6D; tinged with Greyed-Yellow RHS 160B near the apex. Fading, forward surface — Not fading. Fading, back surface — Not fading. Venation — Not visible. Venation color, fully opened, forward surface — Not distinguishable from the petal; coloration is the same as surrounding petal. Venation color, fully opened, back surface — Not distinguishable from the petal; coloration is the same as surrounding petal.

*Labellum*.—Shape — Three-lobed; the shape of the lateral lobes is oblong to near orbicular, and the aspect is involute; the shape of the central lobe is orbicular, and the aspect is heavily undulated. Length — Overall length — Approximately 1.9 cm. Central lobe — Approximately 1.9 cm. Lateral lobes — Approximately 0.6 cm. Width — Overall width — Approximately 1.6 cm. Central lobe — Approximately 1.8 cm. Lateral lobes — Approximately 0.7 cm. Apex — Central lobe — Emarginate. Lateral lobes — Obtuse. Base — Central lobe — Cuneate. Lateral lobes — Cuneate. Margin — Central lobe — Entire; moderately undulated. Lateral lobes — Entire; not undulate. Texture and luster of upper surface — Central lobe — Glabrous and slightly glossy; 3 callosities present. Lateral lobes — Glabrous and slightly glossy. Texture and luster of lower surface — Central lobe — Glabrous and matte. Lateral lobes — Glabrous and matte. Color when opening, forward surface — Central lobe — Yellow-Green near RHS 151A and lighter toward the apex near RHS 151B, with a Greyed-Red central blotch near RHS 178B. Callosities are the same color as the surface. Lateral lobes — Yellow-Green, near RHS 154B. Color when opening, back surface — Central lobe — Yellow-Green near RHS 151B and lighter toward the apex near RHS 151D, with a Greyed-Red central blotch near RHS 178B. Lateral lobes — Yellow-Green, near RHS 154B. Color when fully opened, forward surface — Central lobe — Yellow-Green near RHS 151A and lighter near the margin, near RHS 151B, with a Greyed-Red central blotch near RHS 178B. Callosities are the same color as the surface. Lateral lobes — Yellow-Green, near RHS 150B. Color when fully opened, back surface — Central lobe — Yellow-Green near RHS 151 B and lighter toward the base, near RHS 150B. Lateral lobes — Yellow-Green, near RHS 150B. Fading, forward surface — Not fading. Fading, back surface — Not fading. Venation color, fully opened, forward surface — No venation visible on labellum. Venation color, fully opened, back surface — No venation visible on labellum. Margin — Entire.

*Spurs*.—Quantity — Average of 1. Appearance — Short triangular, in line with central lobe of labellum. Length — Approximately 0.6 cm. Width — Approximately 0.3 cm. Height — Approximately 0.5 cm, at the base. Shape — Short triangular. Apex — Obtuse. Base — Broad Cuneate. Margin — Entire. Texture — Glabrous, matte. Color — Yellow-Green, near RHS 154D.

*Sepals*.—Quantity — Average of 3. Appearance — One dorsal sepal (pointing upright) and two lateral sepals. Length — Dorsal sepal — Approximately 5.3 cm. Lateral sepal — Approximately 5.6 cm. Width — Dorsal sepal — Approximately 4.5 cm. Lateral sepal — Approximately 6.0 cm. Shape — Dorsal sepals are broad ovate and lateral sepals are reniform. Apex — Obtuse. Base — Cuneate. Margin — Entire; strongly undulated. Texture — Glabrous, matte, velvety. Color, when opening — Dorsal sepal, upper side — Yellow, near RHS 4D, and slightly darker towards the margins, in between RHS 8B and 8C; tinged with Greyed-Yellow RHS 160C near the apex; finely dotted Red-Purple at the base, in between RHS 59A and 59B. Dorsal sepal, under side — Yellow, near RHS 3D; tinged with Yellow towards the apex, near RHS 6C. Lateral sepal, upper side — A combination of Green-Yellow, near RHS 1A, and Yellow-Green, near RHS 154B; with margins and apex in between Yellow-Green, RHS 153D, and Greyed-Yellow, RHS 161A; heavily dotted Greyed-Purple, near RHS 183A, throughout the sepal except towards the margins. Lateral sepal, under side — Yellow, in between RHS 2B and 2C, and tinged Greyed-Yellow towards the apex, near RHS 162A. Color, when fully opened — Dorsal sepal, upper side — Yellow near RHS 4C and slightly darker at the margins, near 8C; tinged with Greyed-Yellow RHS 160B near the apex; fine Red-Purple dotting, centrally and towards the base, near RHS 59A to 59B. Dorsal sepal, under side — Yellow near RHS 3D; tinged with Greyed-Yellow towards the apex, in between RHS 160B and 160C. Lateral sepal, upper side — Green-Yellow, near RHS 1A, with margins and apex a combination of Yellow-Green 153D and Greyed-Yellow RHS 161A to 161B; heavily dotted Greyed-Purple, near RHS 183A to 183B, throughout the sepal except towards the margins. Lateral sepal, underside — Yellow, near RHS 2C, and tinged Greyed-Yellow towards the apex, near RHS 162A to 162C. Venation — No visible. Venation color, fully opened, forward surface — Not distinguishable from the petal; coloration is the same as surrounding petal. Venation color, fully opened, back surface — Not distinguishable from the petal; coloration is the same as surrounding petal.

*Pedicels*.—Length — Approximately 5.6 cm. Diameter — Approximately 0.5 cm. Angle — Approximately 80° angle to peduncle. Strength — Very strong. Texture — Glabrous, axially angled with 5 "ribs", axially twisted (due to resupination), glossy. Color — Yellow-green, near RHS 150D, and darker near proximal end, near RHS 150C.

Reproductive organs:

*Stamens, style and stigma fused into column*?.—Yes.

*Column length*.—Approximately 0.7 cm.

*Column diameter*.—Approximately 0.65 cm.

*Column color*.—Yellow-Green, in between RHS 150C and 150D.

*Ovary position*.—Inferior.

*Ovary diameter*.—Approximately 0.4 cm.

*Ovary color*.—Green-Yellow RHS 1D.

*Pollen color*.—Yellow-Orange RHS 14A.

Seed and fruit: No fruit and seed production has been detected to date.

COMPARISONS WITH THE PARENT PLANTS

Plants of the new cultivar 'SPCDW1403' are similar to the seed parent, *Vanda* 'A169', in most horticultural characteristics. However 'SPCDW1403' differs from the seed parent in the following characteristics:

1. 'SPCDW1403' exhibits a light cream-yellow general tonality of the flower, whereas 'A169' exhibits a brighter yellow general tonality of the flower.
2. The flowers of 'SPCDW1403' exhibit a light brown spotting pattern, whereas the flowers of 'A169' lack said pattern.
3. The flowers of 'SPCDW1403' are smaller than those of 'A169'.

Plants of the new cultivar 'SPCDW1403' are similar to the pollen parent, *Vanda* 'JBP', in most horticultural characteristics. However 'SPCDW1403' differs from the pollen parent in the following characteristics:

1. 'SPCDW1403' exhibits a light cream-yellow general tonality of the flower, whereas 'JBP' exhibits a bright yellow general tonality of the flower.
2. The flowers of 'SPCDW1403' exhibit a light brown spotting pattern, whereas the flowers of 'JBP' exhibits a dark brown spotting pattern which is more prominent on the flower.
3. The inflorescence of 'SPCDW1403' are significantly shorter than those of 'JBP'.

COMPARISONS WITH SIMILAR *VANDA* CULTIVARS KNOWN TO THE INVENTOR

'SPCDW1403' is similar in many horticultural characteristics to the commercial variety *Vanda* 'SPCDW0510' (not patented). However 'SPCDW1403' differs from 'SPCDW0510' in the following characteristics:

1. 'SPCDW1403' exhibits light cream-yellow general tonality of the flower, whereas 'SPCDW0510' exhibits a brilliant yellow general tonality of the flower.
2. The flowers of 'SPCDW1403' exhibit a light brown spotting pattern, whereas the flowers of 'SPCDW0510' lack said pattern.
3. The sepals of 'SPCDW1403' are more rounded than those of 'SPCDW0510'.
4. The petal margins of 'SPCDW1403' exhibit a high degree of undulation when compared to the petal margins of 'SPCDW0510'.

'SPCDW1403' is similar to the commercial variety *Vanda* 'SPCDW1406' (U.S. patent application Ser. No. 14/756,938) in that they share the same parentage. However 'SPCDW1403' differs from 'SPCDW1406' in the following characteristics:

1. 'SPCDW1403' exhibits light cream-yellow general tonality of the flower, whereas 'SPCDW1406' exhibits a yellow general tonality of the flower.
2. The flowers of 'SPCDW1403' exhibit a light brown spotting pattern, whereas the flowers of 'SPCDW1406' exhibit a prominent dark brown spotting pattern.
3. 'SPCDW1403' exhibits a light green general tonality of the labellum, whereas 'SPCDW1406' exhibits a light brown general tonality of the labellum.
4. The ovary of 'SPCDW1403' exhibits a darker green general tonality when compared to the general tonality of the ovary of 'SPCDW1406' which is a lighter green.

That which is claimed is:

1. A new and distinct variety of *Vanda* plant named 'SPCDW1403', substantially as described and illustrated herein.

* * * * *